United States Patent
Kumada et al.

(10) Patent No.: US 10,961,422 B2
(45) Date of Patent: Mar. 30, 2021

(54) SURFACE TREATMENT LIQUID, SURFACE TREATMENT METHOD, AND METHOD FOR SUPPRESSING PATTERN COLLAPSE

(71) Applicant: TOKYO OHKA KOGYO CO., LTD., Kawasaki (JP)

(72) Inventors: Shinji Kumada, Kawasaki (JP); Kenji Seki, Kawasaki (JP); Takumi Namiki, Kawasaki (JP)

(73) Assignee: TOKYO OHKA KOGYO CO., LTD., Kawasaki (JP)

( * ) Notice: Subject to any disclaimer, the term of this patent is extended or adjusted under 35 U.S.C. 154(b) by 133 days.

(21) Appl. No.: 16/216,261

(22) Filed: Dec. 11, 2018

(65) Prior Publication Data

US 2019/0194512 A1   Jun. 27, 2019

(30) Foreign Application Priority Data

Dec. 21, 2017  (JP) .............................. JP2017-245116

(51) Int. Cl.
  *C09K 3/18*        (2006.01)
  *H01L 21/306*      (2006.01)
  *C07D 233/58*      (2006.01)

(52) U.S. Cl.
  CPC .............. *C09K 3/18* (2013.01); *H01L 21/306* (2013.01); *C07D 233/58* (2013.01)

(58) Field of Classification Search
  None
  See application file for complete search history.

(56) References Cited

U.S. PATENT DOCUMENTS

| | | | | |
|---|---|---|---|---|
| 3,933,531 A * | 1/1976 | Sawa | ...................... | C23F 11/10 428/470 |
| 4,572,853 A * | 2/1986 | Ikeya | ................... | C08G 59/621 174/110 SR |
| 4,704,234 A * | 11/1987 | Petersen | .............. | C11D 3/0057 134/38 |
| 5,348,590 A * | 9/1994 | Shigemura | ......... | B23K 35/3615 148/23 |
| 5,661,196 A | 8/1997 | Mayer et al. | | |
| 5,695,551 A | 12/1997 | Buckingham et al. | | |
| 5,702,767 A | 12/1997 | Peterson et al. | | |
| 5,872,062 A * | 2/1999 | Hsu | ........................ | C04B 41/009 216/71 |
| 5,960,251 A * | 9/1999 | Brusic | ..................... | C23C 22/68 428/551 |
| 5,982,035 A * | 11/1999 | Tran | .................... | H01L 23/5226 257/750 |
| 6,403,163 B1 | 6/2002 | Fisher et al. | | |
| 2006/0019034 A1 | 1/2006 | Toyoda | | |
| 2006/0127563 A1 | 6/2006 | Toyoda et al. | | |
| 2007/0246134 A1 * | 10/2007 | Hirao | ................... | B23K 35/007 148/528 |
| 2008/0241489 A1 | 10/2008 | Ishibashi et al. | | |
| 2008/0318070 A1 * | 12/2008 | Hirao | ................... | B23K 35/362 428/457 |
| 2011/0195190 A1 * | 8/2011 | Koshiyama | ............... | G03F 7/16 427/284 |
| 2012/0199385 A1 * | 8/2012 | Hirao | ................... | B23K 35/007 174/257 |
| 2013/0052824 A1 | 2/2013 | Hagiwara | | |
| 2014/0131080 A1 * | 5/2014 | Hirao | ................... | C23F 11/165 174/257 |
| 2015/0258707 A1 | 9/2015 | Hirata | | |
| 2019/0203090 A1 * | 7/2019 | Seki | .................. | H01L 21/02057 |

FOREIGN PATENT DOCUMENTS

| | | |
|---|---|---|
| JP | H 07-142349 A | 6/1995 |
| JP | H 11-511900 A | 10/1999 |
| JP | 2010-129932 A | 6/2010 |

OTHER PUBLICATIONS

Office Action issued in U.S. Appl. No. 16/229,883, dated Oct. 29, 2020.

* cited by examiner

*Primary Examiner* — Joseph D Anthony
(74) *Attorney, Agent, or Firm* — Knobbe Martens Olson & Bear LLP

(57) ABSTRACT

A surface treatment liquid capable of hydrophobizing a surface of a treatment target without including a silylation agent, a surface treatment method using the liquid, and a method for suppressing pattern collapse, including surface treatment by the surface treatment method. The liquid contains a nitrogen-containing heterocyclic compound as a water-repelling agent. A compound including one or more hydrocarbon groups which may be substituted with a halogen atom in which a total number of carbon atoms of the one or more hydrocarbon group is three or more, is used as the nitrogen-containing heterocyclic compound. The liquid may include only a nitrogen-containing heterocyclic compound having the above-described predetermined structure, as a water-repelling agent.

12 Claims, No Drawings

SURFACE TREATMENT LIQUID, SURFACE TREATMENT METHOD, AND METHOD FOR SUPPRESSING PATTERN COLLAPSE

This application claims priority to Japanese Patent Application No. 2017-245116, filed Dec. 21, 2017, the entire content of which is incorporated herein by reference.

BACKGROUND OF THE INVENTION

Field of the Invention

The present invention relates to a surface treatment liquid including a water-repelling agent, a surface treatment method using the surface treatment liquid, and a method for suppressing pattern collapse, including surface treatment by the surface treatment method.

Related Art

In recent years, trends toward higher integration and miniaturization of semiconductor devices have grown, and thus progress toward refinement and higher aspect ratios of a resin pattern as an etching mask in etching a substrate and an inorganic pattern produced by etching processes has advanced. In the meantime, however, a problem of so-called pattern collapse has arisen. This pattern collapse is a phenomenon in which when a large number of resin patterns or inorganic patterns are formed on a substrate in parallel, adjacent patterns close in so as to lean on one another, and the patterns are damaged and peeled off from the base depending on the situation. Occurrence of such pattern collapse may cause reduction of the yield and reliability of the product.

This pattern collapse is known to occur when a cleaning liquid is dried in a cleaning process after pattern formation, due to the surface tension of this cleaning liquid. In other words, when the cleaning liquid is removed in a drying step, stress based on the surface tension of the cleaning liquid acts between patterns, whereby pattern collapse occurs.

Conventionally, it has been proposed that hydrophobization (silylation) of a surface of a resin pattern or an inorganic pattern is carried out using a surface treatment liquid including a silylation agent such as N,N-dimethylaminotrimethylsilane (TMSDMA) and hexamethyldisilazane (HMDS) and a solvent so as to prevent pattern collapse (see, for example, Patent Document 1).

Patent Document 1: Japanese Unexamined Patent Application, Publication No. 2010-129932

SUMMARY OF THE INVENTION

With the surface treatment liquid including a silylation agent described in Patent Document 1, generation of a silanol group by hydrolysis of a silylation agent, and hydrophobization (silylation) of a surface of a treatment target by reaction between the generated silanol group and the surface of the treatment target, are carried out. As mentioned above, a silylation agent is easily hydrolyzed in the presence of water, and generates a silanol group. Then, when the silylation agent in the surface treatment liquid is hydrolyzed, the hydrolyzed silylation agents condense. For the above reasons, there has been a problem that a surface treatment liquid including a silylation agent is easily deteriorated over time unless it is stored under low moisture environment.

The present invention has been made considering the above problem, and has an object to provide a surface treatment liquid capable of satisfactorily hydrophobizing a surface of a treatment target without including a silylation agent, a surface treatment method using the surface treatment liquid, and a method for suppressing pattern collapse, including surface treatment by the surface treatment method.

The present inventors have found that the above-mentioned problem can be solved by allowing a surface treatment liquid to contain a nitrogen-containing heterocyclic compound as a water-repelling agent, and using a compound including one or more hydrocarbon groups which may be substituted with a halogen atom as the nitrogen-containing heterocyclic compound, in which a total number of carbon atoms of the one or more hydrocarbon groups is three or more, and have reached the completion of the present invention. Specifically, the present invention provides the followings.

A first aspect of the present invention is a surface treatment liquid including a water-repelling agent (A), wherein the water-repelling agent (A) includes a nitrogen-containing heterocyclic compound having a nitrogen-containing heterocyclic ring only including a carbon atom, a hydrogen atom, and a nitrogen atom, as a main skeleton, and does not include a silylation agent, the nitrogen-containing heterocyclic ring substituted with one or more hydrocarbon groups which may be substituted with a halogen atom, the hydrocarbon group may be substituted with a halogen atom, and a total number of carbon atoms of the one or more hydrocarbon groups is three or more.

A second aspect of the present invention is a surface treatment method including exposing a surface of a treatment target to a surface treatment liquid according to the first aspect, and treating the surface of the treatment target.

A third aspect of the present invention is a method for suppressing collapse of an organic pattern or an inorganic pattern when a surface of a substrate is cleaned with a cleaning liquid, in the substrate having the organic pattern or the inorganic pattern on the surface thereof, the method including treating the surface by the surface treatment method according to the second aspect.

The present invention can provide a surface treatment liquid capable of satisfactorily hydrophobizing a surface of a treatment target without including a silylation agent, a surface treatment method using the surface treatment liquid, and a method for suppressing pattern collapse, including surface treatment by the surface treatment method.

DETAILED DESCRIPTION OF THE INVENTION

<<Surface Treatment Liquid>>

A surface treatment liquid includes a water-repelling agent (A) and a solvent (S). The surface treatment liquid includes, as a water-repelling agent (A), a nitrogen-containing heterocyclic compound having a nitrogen-containing heterocyclic ring only including a carbon atom, a hydrogen atom, and a nitrogen atom as a main skeleton, and does not include a silylation agent. Furthermore, in the nitrogen-containing heterocyclic compound, the nitrogen-containing heterocyclic ring is substituted with one or more hydrocarbon groups which may be substituted with a halogen atom. The hydrocarbon group may be substituted with a halogen atom. In the nitrogen-containing heterocyclic compound, a total number of carbon atoms of the one or more hydrocarbon groups bonded to the nitrogen-containing heterocyclic ring is three or more. When the surface treatment liquid includes a nitrogen-containing heterocyclic compound that satisfies the above-mentioned predetermined requirements, even if the surface treatment liquid does not include a silylation agent, a satisfactory effect of water repellency by surface treatment can be achieved.

More specifically, by the interaction between the nitrogen-containing heterocyclic compound and the surface of the treatment target based on the chemical and physical properties of the nitrogen-containing heterocyclic ring, it is considered that the nitrogen-containing heterocyclic compound can be attached or bonded to the surface of the treatment target. The nitrogen-containing compound attached or bonded to the surface of the treatment target includes one or more hydrocarbon groups which satisfy predetermined requirements and which may be substituted with a halogen atom. The one or more hydrocarbon groups which may be substituted with a halogen atom provide the surface of the treatment target with water repellency. Hereinafter, in this specification, the "nitrogen-containing heterocyclic compound" means a nitrogen-containing heterocyclic compound that satisfies the above-mentioned predetermined requirements unless otherwise noted.

Essential and optional components included in the surface treatment liquid will be explained hereinafter.

<Water-Repelling Agent (A)>

As described above, the surface treatment liquid includes, as a water-repelling agent (A), a nitrogen-containing heterocyclic compound having a nitrogen-containing heterocyclic ring only including a carbon atom, a hydrogen atom, and a nitrogen atom as a main skeleton, and does not include a silylation agent. Furthermore, in the nitrogen-containing heterocyclic compound, the nitrogen-containing heterocyclic ring is substituted with one or more hydrocarbon groups which may be substituted with a halogen atom. The hydrocarbon group may be substituted with a halogen atom. In the nitrogen-containing heterocyclic compound, a total number of carbon atoms of the one or more hydrocarbon groups bonded to the nitrogen-containing heterocyclic ring is three or more.

In other words, in the nitrogen-containing heterocyclic compound, a hydrocarbon group having three or more carbon atoms, for example, an n-propyl group, may not necessarily be bonded to the nitrogen-containing heterocyclic ring. For example, in the nitrogen-containing heterocyclic compound, three methyl groups may be bonded, and a methyl group and an ethyl group may be bonded.

The surface treatment liquid preferably includes substantially only the above-described nitrogen-containing heterocyclic compound as the water-repelling agent (A). Thus, a surface treatment agent that is excellent in stability during storage and that exhibits a satisfactory effect of water repellency can be easily obtained. Examples of the water-repelling agents other than the nitrogen-containing heterocyclic compound include a fluorine-based water-repelling agent, a phosphorus-based water-repelling agent, a titanate-based water-repelling agent, aluminate-based water-repelling agent, and the like. When the water-repelling agent (A) includes substantially only nitrogen-containing heterocyclic compound, it means that the surface treatment liquid does not include a water-repelling agent (A) other than the nitrogen-containing heterocyclic compound exceeding an amount that inhibits the desired effect. Typically, the rate of the mass of the water-repelling agent other than the nitrogen-containing heterocyclic compound to the mass of the water-repelling agent (A) is preferably 5% by mass or less, more preferably 1% by mass or less, further preferably 0.5% by mass or less, particularly preferably 0.1% by mass or less, and the most preferably 0% by mass.

The nitrogen-containing heterocyclic compound has one or more hydrocarbon groups, which may be substituted with a halogen atom, on nitrogen-containing heterocyclic ring as the main skeleton thereof. Hereinafter, in this specification, the "hydrocarbon group" means a hydrocarbon group that may be substituted with a halogen atom unless otherwise noted. A total number of carbon atoms of the one or more hydrocarbon groups bonded to a nitrogen-containing heterocyclic ring is three or more. From the viewpoint that a satisfactory effect of water repellency is achieved, the total number of carbon atoms of the one or more hydrocarbon groups bonded to a nitrogen-containing heterocyclic ring is preferably 4 or more, more preferably 6 or more, and particularly preferably 8 or more. The upper limit of the total number of carbon atoms of the one or more hydrocarbon groups bonded to a nitrogen-containing heterocyclic ring is not particularly limited within a range where the objects of the present invention are not impaired. From the viewpoint that the molecular weight of the nitrogen-containing heterocyclic compound is not excessively large and a satisfactory effect of water repellency can be achieved with a small amount, the upper limit of the total number of carbon atoms of the one or more hydrocarbon groups bonded to the nitrogen-containing heterocyclic ring is preferably 30 or less and more preferably 20 or less.

Furthermore, from the viewpoint that a satisfactory effect of water repellency is achieved, the nitrogen-containing heterocyclic compound is preferably substituted with at least one hydrocarbon group having 3 or more carbon atoms. In the nitrogen-containing heterocyclic compound, preferably, a hydrocarbon group having 4 or more carbon atoms, more preferably, a hydrocarbon group having 6 or more carbon atoms, and particularly preferably, a hydrocarbon group having 8 or more carbon atoms, is bonded to the nitrogen-containing heterocyclic ring. The upper limit of the number of carbon atoms of each hydrocarbon group bonded to the nitrogen-containing heterocyclic ring is not particularly limited. From the viewpoint that the molecular weight of the nitrogen-containing heterocyclic compound is not excessively large, and a satisfactory effect of water repellency can be achieved with a small amount, the number of carbon atoms of each hydrocarbon group bonded to the nitrogen-containing heterocyclic ring is preferably 30 or less, and more preferably 20 or less.

Examples of the halogen atom that can substitute a hydrocarbon group include a fluorine atom, a chlorine atom, a bromine atom, and iodine atom. From the viewpoint that a satisfactory effect of water repellency is easily achieved, the halogen atom is preferably a fluorine atom. From the viewpoint that the molecular weight of the nitrogen-containing heterocyclic compound is not excessively large, and a satisfactory effect of water repellency can be achieved with a small amount, it is preferable that the hydrocarbon group bonded to the nitrogen-containing heterocyclic ring is not substituted with a halogen atom.

In the nitrogen-containing heterocyclic compound, a structure of the hydrocarbon group having 3 or more carbon atoms bonded to the nitrogen-containing heterocyclic ring is not particularly limited. The structure of the hydrocarbon group having 3 or more carbon atoms may be a chain structure, a cyclic structure, a structure including a chain structure and a cyclic structure. The chain structure may be a straight-chain structure, or a branched chain structure. The cyclic structure may be an aliphatic ring structure, an aromatic ring structure, or a ring structure including an aliphatic ring and an aromatic ring. When a surface of the treatment target is treated with the surface treatment liquid, since steric hindrance in the planer direction of a surface to be treated is small and a nitrogen-containing heterocyclic compound is easily attached or bonded to the surface of the treatment target with high density, the structure of the hydrocarbon group having 3 or more carbon atoms is preferably a chain structure, and more preferably a straight-chain structure.

In the nitrogen-containing heterocyclic compound, a hydrocarbon group bonded to the nitrogen-containing heterocyclic ring may include an unsaturated bond.

Preferable examples of the hydrocarbon groups bonded to the nitrogen-containing heterocyclic ring include chain aliphatic hydrocarbon groups such as a methyl group, an ethyl group, an n-propyl group, an isopropyl group, an n-butyl group, an isobutyl group, a sec-butyl group, a tert-butyl group, an n-pentyl group, an n-hexyl group, an n-pentyl group, an n-octyl group, a 2-ethylhexyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, and the like; aromatic hydrocarbon groups such as a phenyl group, an o-tolyl group, an m-tolyl group, an p-tolyl group, an naphthalene-1-yl group, an naphthalene-2-yl group, an o-phenylphenyl group, an m-phenylphenyl group, and a p-phenylphenyl group; alicyclic hydrocarbon groups such as a cyclopropyl group, a cyclobutyl group, a cyclopentyl group, a cyclohexyl group, a cycloheptyl group, a cyclooctyl group, a cyclononyl group, a cyclodecyl group, a tricyclodecyl group, an adamanthyl group, a tetracyclododecyl group, an isobornyl group, and a norbornyl group.

On the nitrogen-containing heterocyclic ring, a substituent other than a hydrocarbon group may be bonded. Types of the substituent other than a hydrocarbon group are not particularly limited within a range where the objects of the present invention are not impaired. Specific examples of the substituent other than a hydrocarbon group include a hydroxyl group, a halogen atom, an alkoxy group, an alkylthio group, an aliphatic acyl group, and a mercapto group, and the like. The number of the substituent other than a hydrocarbon group on the nitrogen-containing heterocyclic ring is not particularly limited. Typically, the number of the substituent other than a hydrocarbon group is preferably 3 or less, more preferably 2 or less, and particularly preferably 1 or 0.

Types of the nitrogen-containing heterocyclic ring constituting a main skeleton of the nitrogen-containing heterocyclic compound are not particularly limited as long as a desired surface treatment effect can be obtained. The nitrogen-containing heterocyclic ring may be an aliphatic ring, or an aromatic ring. Since chemical stability or thermal stability of the nitrogen-containing heterocyclic compound is satisfactory, and an effect of water repellency is satisfactory, the nitrogen-containing heterocyclic ring is preferably an aromatic ring.

The nitrogen-containing heterocyclic ring may be a monocyclic ring or a polycyclic ring. The polycyclic ring may be a condensed ring in which two or more monocyclic rings condense, or a polycyclic ring in which two or more monocyclic rings or condensed rings are bonded by a single bond or a linking group. When the nitrogen-containing heterocyclic ring is a polycyclic ring, at least one of two or more monocyclic rings constituting the polycyclic ring may be a nitrogen-containing heterocyclic ring. Examples of the linking group include an alkylene group having 1 or more and 4 or less carbon atoms, a carbonyl group, an ester bond, a carbonate bond, an ether bond, a sulfonyl group, a sulfide bond, a disulfide bond, an amino group (—NH—), and the like. From the viewpoint of easiness in obtaining a nitrogen-containing heterocyclic compound at a low price or synthesis, the nitrogen-containing heterocyclic ring is preferably a monocyclic ring.

Specific examples of the nitrogen-containing heterocyclic ring include nitrogen-containing five-membered rings such as a pyrrolidine ring, a pyrazolidine ring, an imidazolidine ring, a triazolidine ring, a tetrazolidine ring, a pyrroline ring, a pyrazoline ring, an imidazoline ring, a triazoline ring, a tetryzoline ring, a pyrrole ring, a pyrazole ring, an imidazole ring, a triazole ring, and a tetrazole ring; nitrogen-containing six-membered rings such as a piperidine ring, a piperidyne ring, a piperazine ring, a triazinane ring, a tetrazinane ring, a pentazinane ring, a pyridine ring, a pyridazine ring, a pyrimidine ring, a pyrazine ring, a triazine ring, a tetrazine ring, and pentazine ring; nitrogen-containing seven-membered rings such as an azepane ring, a diazepane ring, triazepane ring, a tetrazepane ring, an azepine ring, a diazepine, and a triazepin; nitrogen-containing condensed polycyclic rings such as an indole ring, an indolenine ring, an indoline ring, an isoindole ring, an isoindolenine, an isoindoline ring, a benzimidazole ring, an indolizine ring, a purine ring, an indolizine ring, a benzodiazepine ring, a quinoline ring, an isoquinoline ring, a quinolizidine ring, a quinoxaline ring, a cinnoline ring, a quinazoline ring, a phthalazine ring, a naphthyridine ring, and pteridine ring.

From the viewpoint that a satisfactory effect of water repellency is achieved, the nitrogen-containing heterocyclic ring in the nitrogen-containing heterocyclic compound is preferably a nitrogen-containing five-membered ring or a condensed ring including a nitrogen-containing five-membered ring. Examples of the nitrogen-containing five-membered ring include the above-mentioned nitrogen-containing five-membered ring. The condensed ring including the nitrogen-containing five-membered ring is preferably a condensed ring of the nitrogen-containing five-membered ring and a cyclopentane ring, a cyclohexane ring, a benzene ring, or a pyridine ring. From the viewpoint that satisfactory effect of water repellency is achieved, the nitrogen-containing five-membered ring is preferably an imidazole ring; and the condensed ring including the nitrogen-containing five-membered ring is preferably a condensed ring including an imidazole ring, and more preferably a benzimidazole ring.

In the nitrogen-containing heterocyclic compound, it is preferable that the above-described hydrocarbon group is bonded to the carbon atom constituting a nitrogen-containing heterocyclic ring. It is considered to be because a nitrogen atom in the nitrogen-containing heterocyclic ring has an influence on attaching or bonding of the nitrogen-containing heterocyclic compound to a surface of a treatment target.

Among the above-described nitrogen-containing heterocyclic compounds, since availability and synthesis thereof are easy, solubility of the surface treatment liquid is excellent, and a satisfactory effect of water repellency is achieved, 2-alkylimidazole having an alkyl group having 3 or more and 20 or less carbon atoms at position 2, and 2-alkyl benzimidazole having an alkyl group having 3 or more and 20 or less carbon atoms at position 2 are preferable. From the viewpoint that the effect of water repellency is particularly satisfactory, 2-alkylimidazole having an alkyl group having 3 or more and 20 or less carbon atoms at position 2 is more preferable.

Suitable specific examples of 2-alkylimidazole having an alkyl group having 3 or more and 20 or less carbon atoms at position 2 include 2-n-propylimidazole, 2-isopropylimidazole, 2-n-butylimidazole, 2-isobutylimidazole, 2-sec-butylimidazole, 2-tert-butylimidazole, 2-n-pentylimidazole, 2-n-hexylimidazole, 2-n-pentylimidazole, 2-n-octylimidazole, 2-(2-ethylhexyl)imidazole, 2-n-nonylimidazole, 2-n-decylimidazole, 2-n-undecylimidazole, 2-n-dodecylimidazole, 2-n-tridecylimidazole, 2-n-tetradecylimidazole, 2-n-pentadecylimidazole, 2-n-hexadecylimidazole, 2-n-heptadecylimidazole, 2-n-octadecylimidazole, 2-n-nonadecylimidazole, and 2-n-icosylimidazole.

Suitable specific examples of 2-alkyl benzimidazole having an alkyl group having 3 or more and 20 or less carbon atoms at position 2 include 2-n-propylbenzimidazole, 2-isopropylbenzimidazole, 2-n-butylbenzimidazole, 2-isobutylbenzimidazole, 2-sec-butylbenzimidazole, 2-tert-butylbenzimidazole, 2-n-pentylbenzimidazole, 2-n-hexylbenzimidazole, 2-n-pentylbenzimidazole, 2-n-octylbenzimidazole, 2-(2-ethylhexyl)imidazole, 2-n-nonylbenzimidazole, 2-n-decylbenzimidazole, 2-n-undecylbenzimidazole, 2-n-dodecylbenzimidazole, 2-n-tridecylbenzimidazole, 2-n-tetradecylbenzimidazole, 2-n-pentadecylbenzimidazole, 2-n-hexadecylbenzimidazole, 2-n-heptadecylbenzimidazole, 2-n-octadecylbenzimidazole, 2-n-nonadecylbenzimidazole, and 2-n-icosylbenzimidazole.

When a surface of a treatment target is made of tungsten and/or titanium nitride, it may have been difficult to provide a surface of a treatment target with water repellency by a surface treatment liquid including a water-repelling agent such as a silylation agent. However, the surface treatment liquid including a water-repelling agent (A) described above can satisfactorily provide the surface made of tungsten and/or titanium nitride with water repellency. Therefore, the surface treatment liquid including the water-repelling agent (A) and a solvent (S) described above can be suitably used for surface treatment of a surface made of tungsten and/or titanium nitride in least a part.

The content of the water-repelling agent (A) in the surface treatment liquid is not particularly limited as long as a desired effect of water repellency is achieved. The content of the water-repelling agent (A) in the surface treatment liquid is preferably 0.1% by mass or more and 30% by mass or less, more preferably 0.5% by mass or more and 20% by mass or less, and particularly preferably 1% by mass or more and 10% by mass or less.

<Solvent (S)>

A surface treatment liquid contains a solvent (S). The solvent (S) is not particularly limited and any conventionally well-known solvents can be used as long as they can dissolve a water-repelling agent (A) and give less damage to the surface of the treatment target as a subject to be treated.

The solvent (S) is not particularly limited, and example thereof include glycol monoethers such as ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, diethylene glycol monomethyl ether, diethylene glycol monoethyl ether, diethylene glycol monopropyl ether, and diethylene glycol monophenyl ether; glycol diethers such as ethylene glycol dimethyl ether, ethylene glycol diethyl ether, ethylene glycol dipropyl ether, propylene glycol dimethyl ether, propylene glycol diethyl ether, propylene glycol dipropyl ether, diethylene glycol dimethyl ether, diethylene glycol diethyl ether, and diethylene glycol dipropyl ether; glycol monoacetates such as ethylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, and diethylene glycol monoethyl ether acetate; monoether monoacetates of diols, such as diethylene glycol monopropyl ether acetate, diethylene glycol monobutyl ether acetate, diethylene glycol monophenyl ether acetate, propylene glycol monomethyl ether acetate, propylene glycol monoethyl ether acetate, propylene glycol monopropyl ether acetate, 2-methoxybutyl acetate, 3-methoxybutyl acetate, 4-methoxybutyl acetate, 2-methyl-3-methoxybutyl acetate, 3-methyl-3-methoxybutyl acetate, 3-ethyl-3-methoxybutyl acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, and 4-methyl-4-methoxypentyl acetate; ketones such as acetone, methyl ethyl ketone, diethyl ketone, methyl isobutyl ketone, ethyl isobutyl ketone, and cyclohexanone; esters such as methyl propionate, ethyl propionate, propyl propionate, isopropyl propionate, 2-hydroxymethyl propionate, 2-hydroxyethyl propionate, 2-hydroxy-2-methyl, methyl-3-methoxypropionate, ethyl-3-methoxypropionate, ethyl-3-ethoxypropionate, ethyl-3-propoxypropionate, propyl-3-methoxypropionate, isopropyl-3-methoxypropionate, ethoxyethyl acetate, oxyethyl acetate, methyl 2-hydroxy-3-methylbutanoate, methyl acetate, ethyl acetate, propyl acetate, isopropyl acetate, butyl acetate, isoamyl acetate, methyl carbonate, ethyl carbonate, propyl carbonate, butyl carbonate, methyl pyruvate, ethyl pyruvate, propyl pyruvate, butyl pyruvate, methyl acetoacetate, ethyl acetoacetate, benzyl acetate, ethyl benzoate, diethyl oxalate, diethyl maleate, and γ-butyrolactone; ethers such as diethyl ether, dipropyl ether, dibutyl ether, dihexyl ether, benzyl methyl ether, benzyl ethyl ether, and tetrahydrofuran; aromatic compounds such as benzene, toluene, xylene, ethylbenzene, cresol, and chlorobenzene; aliphatic alcohols such as methanol, ethanol, n-propanol, isopropanol, n-butanol, n-hexanol, and cyclohexanol; glycols such as ethylene glycol, diethylene glycol, propylene glycol, and dipropylene glycol; glycerol; and aprotic polar organic solvents such as N,N,N',N'-tetramethylurea, N-methyl-2-pyrrolidone, N,N-dimethylformamide, N,N-dimethylacetamide, hexamethylphosphoramide, 1,3-dimethyl-2-imidazolidinone, and dimethyl sulfoxide. Furthermore, the solvent may be a hydrocarbon-based solvent of aliphatic hydrocarbon such as n-hexane, cyclohexane, n-heptane, n-octane, n-nonane, methyl octane, n-decane, n-undecane, and n-dodecane, or may be a terpene-based solvent including terpinenes such as menthanes such as p-menthane, o-menthane, and m-menthane, diphenyl menthane, limonene, α-terpinene, β-terpinene, and γ-terpinene; pinenes such as bornane, norbornane, pinane, α-pinene, and β-pinene; monoterpenes such as carane and longifolene; and diterpenes such as abietane, and the like.

Among them, from the viewpoint of a surface treatment effect and displaceability with a cleaning liquid, glycol monoether, monoether monoacetate of diols, aliphatic alcohols, and esters are preferable. These solvents can be used alone or in combination of at least two thereof.

<Other Components>

A surface treatment liquid may include various additives together with the water-repelling agent (A) and the solvent (S) within the scope in which the object of the present invention is not hindered. Examples of the additives include a surfactant, a pH adjustor, a viscosity modifier, an antifoamer, a coloring agent, and the like.

A surface treatment liquid is prepared by uniformly mixing and dissolving the above-described water-repelling agent (A), solvent (S), and the other components as necessary.

<<Surface Treatment Method>>

Hereinafter, a surface treatment method will be explained. The surface treatment method exposes a surface of a treatment target to the above-described surface treatment liquid, and treats the surface of the treatment target. As described above, treatment using the above-described surface treatment liquid provides the surface of the treatment target with water repellency. The treatment target is not particularly limited as long as it can be made water repellent by the above-described surface treatment liquid. The shape and size of the treatment target are not particularly limited. Furthermore, material of a surface to be treated with the surface treatment liquid is not also particularly limited. The material of a surface to be treated with a surface treatment liquid may be an inorganic material or an organic material such as resin.

Typical examples of the treatment target include a substrate. As the substrate, a substrate at least a part of which is made of one or more materials selected from the group consisting of silicon, silicon oxide, silicon nitride, titanium nitride, and tungsten is preferable. Among these materials, more preferred is tungsten and/or titanium nitride, because the water repellency by a surface treatment liquid including a water-repelling agent such as a silylation agent is difficult, and an effect of the present invention can be satisfactorily exhibited.

As the method of exposing a treatment target such as a substrate to the surface treatment liquid, any conventionally well-known methods can be used without limitation. Examples of the method include a method of bringing a surface treatment liquid into contact with a surface of a treatment target by a spray method, a spin coating method, a dip coating method, a roll coating method, and the like. Treatment time for exposing the treatment target such as a substrate to the surface treatment liquid is preferably 1 second or more and 60 seconds or less. In addition, after this surface treatment, the contact angle of water on the surface preferably becomes 40 degrees to 120 degrees, and more preferably 60 degrees to 100 degrees.

A temperature of the surface treatment liquid at the time of surface treatment is not particularly limited as long as a desired effect of water repellency is achieved. Since composition change of the surface treatment liquid is not likely to occur due to volatilization and degradation or the like of the water-repelling agent (A) and the solvent (S), and a desired effect of water repellency is likely to be achieved stably, the temperature of the surface treatment liquid at the time of surface treatment is, for example, 0° C. or more and 40° C. or less, preferably 5° C. or more and 35° C. or less, more preferably 10° C. or more and 30° C. or less, that is, a temperature around a room temperature.

After a surface of the treatment target is exposed to the surface treatment liquid, when an organic solvent or the like contained in the surface treatment liquid remains on the surface of the treatment target, such a remaining substance is preferably removed. The methods of removing a remaining substance are not particularly limited. Examples of the methods include a method of blowing gas such as nitrogen or dry air over the surface of the treatment target, a method of heating the substrate up to an appropriate temperature depending on the boiling point of a solvent to be removed, and a method of cleaning with a conventionally well-known cleaning liquid (for example, water, isopropyl alcohol, an activator rinse, SPM, APM, or the like) which have been used in cleaning process. Note here that it is preferable from the viewpoint of throughput that the surface treatment and the cleaning process are preferably continuous processes. As a result, for the surface treatment liquid, it is preferable to select a surface treatment liquid that is excellent in displaceability with the cleaning liquid.

Note here that depending on the applications of use of the treatment target, it may be desirable that after water repellency is provided by the surface treatment, water repellency (or hydrophilic property) of the surface of the treatment target is brought closer to the level before surface treatment. Herein, when the surface treatment is carried out using the above-described surface treatment liquid, by heating the surface treated treatment target at a low temperature, for example, about 80° C. or higher and 250° C. or lower, and preferably about 100° C. or higher and 200° C. or lower, for about one minute or more and one hour or less, the water repellency (or hydrophilic property) of the surface of the treatment target can be brought closer to the water repellency (or hydrophilic property) before the surface treatment. Such a method can carry out treatment of bringing the water repellency (or hydrophilic property) of the surface of the treatment target closer to the water repellency (or hydrophilic property) before the surface treatment with high throughput. Furthermore, since the heating temperature is low, the above-mentioned treatment can be carried out with small energy required to heating and at a low cost. The heat treatment of the treatment target mentioned above may be carried out in the air, or under atmosphere of inert gas such as nitrogen. The above-mentioned heat treatment is preferably carried out under atmosphere of inert gas such as nitrogen because the surface of the treatment target is not easily oxidized.

<<Method for Suppressing Pattern Collapse>>

A pattern collapse suppressing method is a method for suppressing collapse of an organic pattern or an inorganic pattern when a surface of a substrate is cleaned with a cleaning liquid, in the substrate having the organic pattern or the inorganic pattern on the surface thereof. Such a method for suppressing pattern collapse includes surface-treating the surface of the substrate by the above-described surface treatment method. Hereinafter, the pattern collapse will be explained.

In recent years, trends toward higher integration and refinement of semiconductor devices have grown, and thus progress toward refinement and higher aspect ratios of the inorganic pattern such as silicone pattern and organic pattern such as resist pattern have advanced. In the meantime, however, a problem of so-called pattern collapse has arisen. This pattern collapse is a phenomenon in which when a large number of patterns are formed on a substrate in parallel, adjacent patterns close in so as to lean on one another, and the patterns are damaged from the base depending on the situation. When such pattern collapse occur, desired products cannot be obtained, which may cause reduction of the yield and reliability of the product.

The pattern collapse is known to occur when a rinsing liquid is dried in rinse treatment after pattern formation, due to the surface tension of the rinsing liquid. In other words, when the rinsing liquid is removed in a drying step, stress based on the surface tension of the rinsing liquid acts between patterns, whereby pattern collapse occurs.

Herein, force F acting between patterns of the inorganic pattern in the drying step after rinsing is represented by the following formula (I). Herein, γ represents surface tension of a rinsing liquid, θ represents a contact angle of a rinsing liquid, A represents the aspect ratio of the inorganic pattern, and D represents a distance between the inorganic pattern side walls.

$$F = 2\gamma \cdot \cos\theta \cdot A/D \quad (I)$$

Therefore, when the surface of the organic pattern or the inorganic pattern can be provided with water repellency, and when a contact angle of the rinsing liquid can be increased (cos θ can be reduced), force acting between patterns in the drying step after rinsing can be reduced, and pattern collapse can be prevented. Consequently, when a surface of a substrate having an organic pattern or an inorganic pattern on the surface thereof is surface-treated so as to provide water repellency by the above-described surface treatment method, pattern collapse of the organic pattern or the inorganic pattern is effectively suppressed.

The above-described surface treatment method can satisfactorily provide a surface made of tungsten and/or titanium nitride with water repellency. Therefore, it is preferable that at least a part of the surface of the substrate having an organic pattern or an inorganic pattern is tungsten and/or titanium nitride. In the substrate having a pattern made of tungsten and/or titanium nitride on the surface thereof, pattern collapse has not been easily suppressed by a method using a silylation agent or the like. However, with the above-described method for suppressing pattern collapse, the surface of the substrate is satisfactorily provided with water repellency also on the substrate having a pattern made of tungsten and/or titanium nitride on the surface thereof, thus satisfactorily suppressing pattern collapse.

EXAMPLES

Hereinafter, the present invention will be explained in more detail by way of Examples. Note here that the present invention is not limited to the following Examples.

Example 1

2-n-undecylimidazole was dissolved in propylene glycol monomethyl ether such that the concentration was 3% by mass to obtain a surface treatment liquid of Example 1.

Comparative Example 1

1,1,1,3,3,3-hexamethyldisilazane (silylation agent) and imidazole were dissolved in propylene glycol monomethyl ether acetate such that the concentration of 1,1,1,3,3,3-hexamethyldisilazane (silylation agent) was 10% by mass and the concentration of imidazole was 4.2% by mass to obtain a surface treatment liquid of Comparative Example 1.

Surface treatment for a tungsten substrate and a titanium nitride substrate was carried out using the surface treatment liquids of Example 1 and Comparative Example 1.

Firstly, each substrate was dipped in an HF aqueous solution having a concentration of 1% by mass at 25° C. for one minute to remove a natural oxide film on the surface of each substrate. After dipping, each substrate was cleaned with ion exchange distilled water and blown with nitrogen so as to obtain a dried substrate.

Next, a water contact angle of each substrate was measured using Dropmaster 700 (manufactured by Kyowa Interface Science Co., Ltd.). Specifically, a droplet of pure water (1.8 μL) was dropped onto the surface of the substrate, and the contact angle 10 seconds after dropping was measured.

The water contact angle of each substrate before surface treatment is shown in Table 1.

The dried substrate was dipped in the surface treatment liquid of Example 1 or in surface treatment liquid of Comparative Example 1 at 25° C. for 40 seconds, and then, the substrate was dipped and cleaned in isopropyl alcohol for one minute. The cleaned substrate was blown with nitrogen to obtain a surface-treated substrate. In each of the obtained substrates, a water contact angle was measured. The water contact angle of each substrate after surface treatment was shown in Table 1.

TABLE 1

| | | Water contact angle (°) | |
|---|---|---|---|
| | Types of surface treatment liquid | Tungsten substrate | Titanium nitride substrate |
| Substrate before surface treatment | — | 41.5 | 16.1 |
| Substrate after surface treatment | Example 1 | 93.9 | 76.6 |
| | Comparative Example 1 | <10 | <10 |

Example 1 shows that use of the surface treatment liquid including a nitrogen-containing heterocyclic compound having a predetermined structure as a water repellent agent can satisfactorily provide surfaces of substrates made of various materials with water repellency. Furthermore, comparison between Example 1 and Comparative Example 1 shows that use of the surface treatment liquid including a nitrogen-containing heterocyclic compound having a predetermined structure as a water repellent agent can satisfactorily provide surfaces of a tungsten substrate and a titanium nitride substrate, which are not easily provided with water repellency by a silylation agent like 1,1,1,3,3,3-hexamethyldisilazane, with water repellency.

Example 2, Example 3, Comparative Example 2, and Comparative Example 3

Surface treatment liquids of Examples 2 and 3, and Comparative Examples 2 and 3 were obtained in the same manner as in Example 1 except that 2-n-undecylimidazole was changed to the water-repelling agents of types described in Table 2. A tungsten substrate and a silicon nitride substrate were subjected to surface treatment in the same manner as in Example 1 using the resultant surface treatment liquid of Example 2. Furthermore, a silicon nitride substrate was subjected to surface treatment in the same manner as in Example 1 using the resultant surface treatment liquids of Example 3, Comparative Examples 2 and 3. The water contact angle of each substrate after surface treatment was measured in the same manner as in Example 1. The measured water contact angles are shown in Table 2.

TABLE 2

| | | Water contact angle (°) | |
|---|---|---|---|
| | Types of water-repelling agent | Tungsten substrate | Titanium nitride substrate |
| Example 1 | 2-n-undecylimidazole | 93.9 | 76.6 |
| Example 2 | 2-n-butylimidazole | 85.3 | 52.8 |
| Example 3 | 2-nonylbenzimidazole | — | 28.5 |
| Comparative Example 2 | 2-methylimidazole | — | 11.6 |

TABLE 2-continued

| | | Water contact angle (°) | |
|---|---|---|---|
| | Types of water-repelling agent | Tungsten substrate | Titanium nitride substrate |
| Comparative Example 3 | Imidazole | — | 11.5 |

According to Examples 1 to 3, when the surface treatment liquid includes a nitrogen-containing heterocyclic compound having a predetermined structure substituted with a hydrocarbon group, the surface of the substrate as a treatment target can be satisfactorily provided with water repellency even if the surface treatment liquid does not include a water-repelling agent like a silylation agent. On the other hand, according to Comparative Examples 2 and 3, even when the surface treatment liquid includes a nitrogen-containing heterocyclic compound, when the nitrogen-containing heterocyclic compound is not substituted with a hydrocarbon group, or when the number of carbon atoms of a hydrocarbon group as a substituent is 1, the surface of the substrate as a treatment target cannot be easily provided with water repellency.

What is claimed is:

1. A method for suppressing collapse of an organic pattern or an inorganic pattern when a surface of a substrate is cleaned with a cleaning liquid, wherein the organic pattern or the inorganic pattern is present on the surface of the substrate, a plurality of the organic patterns or the inorganic patterns are present on the substrate, and the proximity of adjacent patterns to one another causes the adjacent patterns to lean on one another, the method comprising exposing the surface of the substrate to a surface treatment liquid comprising a water-repelling agent (A), wherein the water-repelling agent (A) includes a nitrogen-containing heterocyclic compound having a nitrogen-containing heterocyclic ring only including a carbon atom, a hydrogen atom, and a nitrogen atom as a main skeleton, and the water-repelling agent (A) does not include a silylation agent, the nitrogen-containing heterocyclic ring is substituted with one or more hydrocarbon groups which may be substituted with a halogen atom, and a total number of carbon atoms of the one or more hydrocarbon groups is three or more.

2. The method according to claim 1, wherein the pattern present on the substrate includes tungsten or titanium nitride.

3. The method according to claim 1, wherein the water-repelling agent (A) includes substantially only the nitrogen-containing heterocyclic compound.

4. The method according to claim 1, wherein the nitrogen-containing heterocyclic compound is substituted with at least one hydrocarbon group having three or more carbon atoms.

5. The method according to claim 4, wherein the hydrocarbon group having three or more carbon atoms is a chain aliphatic hydrocarbon group.

6. The method according to claim 1, wherein the nitrogen-containing heterocyclic ring is an aromatic ring.

7. The method according to claim 1, wherein the nitrogen-containing heterocyclic ring is a nitrogen-containing five-membered ring, or a condensed ring including a nitrogen-containing five-membered ring.

8. The method according to claim 7, wherein the nitrogen-containing heterocyclic ring is an imidazole ring, or a condensed ring including an imidazole ring.

9. The method according to claim 1, wherein the hydrocarbon group is bonded to carbon atoms comprising the nitrogen-containing heterocyclic ring.

10. The method according to claim 8, wherein the nitrogen-containing heterocyclic compound is 2-alkylimidazole having an alkyl group having 3 or more and 20 or less carbon atoms at position 2.

11. The method according to claim 2, wherein the pattern includes tungsten.

12. The method according to claim 1, wherein at least a part of the surface of the substrate is made of one or more materials selected from the group consisting of silicon, silicon oxide, silicon nitride, titanium nitride, and tungsten.

* * * * *